(12) United States Patent
Russo-Rodriguez et al.

(10) Patent No.: US 6,407,289 B1
(45) Date of Patent: Jun. 18, 2002

(54) SYNTHESIS OF $N^4$, $N^4$-DIPHENYL-$N^4$,$N^4$-DI-M-TOLYL-BIPHENYL-4,4'-DIAMINE FROM AN UNSYMMETRICAL AMINE

(75) Inventors: Sandra Russo-Rodriguez, Laredo, TX (US); Jeffrey M. Sullivan, Loveland, CO (US)

(73) Assignee: Boulder Scientific Co., Mead, CO (US)

( * ) Notice: Subject to any disclaimer, the term of this patent is extended or adjusted under 35 U.S.C. 154(b) by 0 days.

(21) Appl. No.: 09/492,327

(22) Filed: Jan. 27, 2000

(51) Int. Cl.[7] ............................................. C07C 211/00
(52) U.S. Cl. ....................... 564/309; 564/307
(58) Field of Search .................................. 564/301, 359, 564/405, 433, 432, 434

(56) References Cited

PUBLICATIONS

Cas Online Printout 120:284968 rn 154924–90–0, Jul. 1993.*

* cited by examiner

*Primary Examiner*—Samuel Barts
(74) *Attorney, Agent, or Firm*—Edward S. Irons

(57) ABSTRACT

Novel (4-halophenyl) biphenyl tolyl amines are described.

10 Claims, No Drawings

SYNTHESIS OF N⁴, N⁴-DIPHENYL-N⁴,N⁴-DI-M-TOLYL-BIPHENYL-4,4'-DIAMINE FROM AN UNSYMMETRICAL AMINE

FIELD OF THE INVENTION

This invention relates to the nickel catalyzed formation of novel unsymmetrical tertiary amines. More particularly, the invention relates to (4-halo-phenyl)-phenyl-m-tolyl-amines     (I)

which may be converted to

N⁴,N⁴'-diphenyl-N⁴,N⁴-di-m-tolyl-biphenyl-4,4'diamine     (II)

by nickel catalyzed coupling.

BACKGROUND OF THE INVENTION

It is known to produce (II) by palladium catalyzed amination using m-methyldiphenylamine, 4,4'-dibromobiphenyl and tri-tert-butyl phosphine. See Yamamoto, T., et al., *Tetrahedron Letters* (1998) 39:2367–2370. It is also known to produce (II) by reaction of m-methyldiphenyl amine with 4,4'-diiodobiphenyl under copper powder in potassium hydroxide or other bases in high boiling solvents at 150–200° C. See, e.g., U.S. Pat. No. 4,764,625. 1,10-phenanthroline has been used to ligate copper and the use of Cu(I) salts has been reported to reduce the temperature of this reaction to 125° C. See Goodbrand, *J. Org. Chem.* (1999) 64:4290 and U.S. Pat. Nos. 5,654,482; 5,648,539; 5,648,542; 5,705,697; 5,723,669 and 5,723,671. Coupling of chlorobenzene to afford biphenyl and 4-chloroaniline to afford 4,4'-diaminobiphenyl using $NiCl_2$, triphenylphosphine, zinc and DMF with and without 2,2'-bipyridyl is described in *J. Org. Chem.* (1986) 51:2367–2370. U.S. Pat. No. 4,263,466 describes a method for coupling aryl chlorides in which a nickel catalyst is generated in situ from nickel salts and excess reducing agents.

In general, a problem exists in that prior art procedures for producing (II) and similar compounds entail the use of biphenyl starting material including expensive dihalobiphenyls and harsh high temperature conditions.

A need exists for a more cost effective method for producing such compounds.

There is a particular need for a mild, low temperature nickel catalyzed synthesis of an intermediate which may be converted to compounds typified by (II).

SUMMARY OF THE INVENTION

Pursuant to this invention, the biphenyl moiety of compounds such as (II) is assembled after the amine moieties are in place. A novel intermediate (I) is synthesized. The intermediate is then coupled in a mild nickel catalyzed reaction. A novel intermediate, e.g., unsymmetrical, triarylamine (4-halo-phenyl)phenyl-m-tolyl amine (I) is first synthesized from cheap building blocks, typically m-toluidine, bromobenzene, and 1,4 bromo-chlorobenzene to yield tri-aryl amine chloride (I). The synthesis is accomplished via two, sequential palladium catalyzed aminations in one pot. The compound (I) may be crystallized in good yield, e.g., above 80% yield, and high purity, e.g., 95% purity. (II) is produced by nickel catalyzed coupling of (I).

DETAILED DESCRIPTION OF THE INVENTION

Synthesis of (I) (4-Chloro-Phenyl-M-Tolyl Amines)

In the first step, the pot is charged under nitrogen with palladium acetate, tri-tert-butyl phosphine and dry deoxygenated toluene. A first reaction mixture of a red color results. Bromobenzene, sodium t-butoxide and m-toluidine are added sequentially under nitrogen. The reaction is heated with stirring under reflux for a time sufficient, e.g., 1 to 2.5 hours, to produce a reaction mixture containing 95–97% of m-methyl diphenyl amine. 1,4-bromo chlorobenzene and sodium t-butoxide are then added, and the reaction is stirred to reflect overnight to afford (I). The reaction is illustrated by Equation 1:

Equation 1

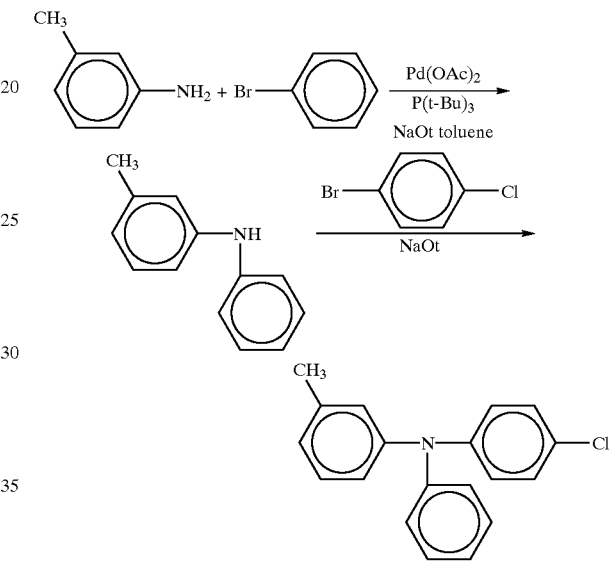

In Equation 1, m-toluidine may be replaced by an compound of the formula:

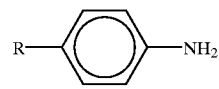

in which R is an ortho, meta, or para $C_1$ to $C_{10}$ alkyl substituent,

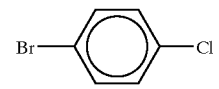

may be replaced by any compound of the formula:

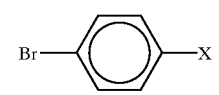

in which X is any halogen or triflate.

EXAMPLE 1

Preparation of (4-chloro-phenyl)-phenyl-m-tolyl amine (I)

Under nitrogen, a flask is charged with 138 mg (0.0006 mol) of palladium acetate, 0.48 g (0.002 mol) of tri-tertbutylphosphine, 180 grams of dry, deoxygenated toluene. The solution is stirred for 5 minutes until the pale yellow color changed to a red color. The other reagents are added sequentially under nitrogen: 22 mL (0.2 mol) of bromobenzene, 25.3 g (0.26 mol) of sodium t-butoxide and m-toluidine (22 mL, 0.2 mol). The reaction is heated with stirring to reflux for 2.5 hours, at the end of which it was cooled down and analyzed by GC/MS to contain 95–97% of m-methyldiphenylamine. 25.8 g (0.26 mol) of sodium t-butoxide and 38.8 g (0.2 mol) of 1,4-bromochlorobenzene are added; the reaction is filled with nitrogen, and heated to reflux with stirring for 18 hours. The reaction is cooled, water is added, extract the aqueous with toluene. The combined organic layers are dried over sodium sulfate, filtered through a pad of neutral alumina, and the filtrate is distilled to remove the bulk of the solvent. The concentrated solution is treated with MeOH slowly with stirring. The solid is collected to afford 50 g (83%) of (4-chloro-phenyl)-phenyl-m-tolyl amine as an off-white solid.

Synthesis of (II)

Coupling of (I) to produce (II) may be accomplished in two steps, preferably in one pot.

In a first step, a dry nitrogen filled pot is charged with zinc powder, triphenyl phosphine 2,2' bipyridyl, anhydrous NiCl$_2$ deoxygenated DMF and activated molecular sieves. Presently preferred coupling conditions are 0.5 eq NiCl$_2$, 0.05 eq 2,2' pyridyl, 0.26 eq triphenylphosphine, 1.5 eq zinc in 60–70° C. DMF. The mixture is heated under conditions effective to produce a color change from gray to dark brown. Appropriate conditions include heating at a temperature of 50° C. to 100° C., preferably about 65° C., for about 10–15 minutes.

Thereafter, in a second step, the pot temperature is maintained at about 50–60° C., a solution of (4-chloro-phenyl)-phenyl-m-tolyl amine (I) in DMF is added dropwise. The reaction mixture is maintained at about 60–65° C. with stirring, preferably until complete consumption of (I) as may be evidenced by TLC analysis is achieved. The reaction mixture may then be diluted with an inert diluent, such as dichloromethane, diethyl ether, or toluene, and filtered to remove excess zinc and solids. The filtrate is washed with water several times resulting in the formation of an aqueous layer and a dichloromethane layer which is separated, treated with silica gel, filtered, and the filtrate is treated with neutral alumina. The product (I) is recovered by crystallization.

The reaction is illustrated by Equation 2:

Equation 2

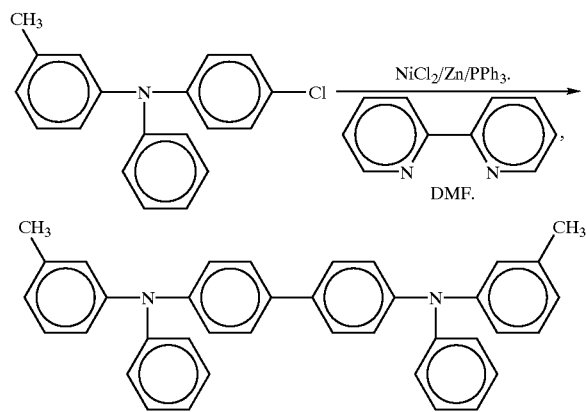

In Equation 2, the reactant (a) may be replaced by a similar compound in which —CH$_3$ is replaced by any ortho, meta, or para C$_1$ to C$_{10}$ alkyl group, and Cl is replaced by bromine or fluorine.

EXAMPLE 2

Preparation of N$^4$,N$^{4'}$-Diphenyl-N$^4$,N$^{4'}$-di-m-tolyl-biphenyl-4,4'-diamine:

Charge a dry, nitrogen filled flask with 4.9 g (0.07 mol of zinc powder), 3.4 g (0.01 mol) of triphenylphosphine. 0.4 g (0.002 mol) of 2,2'-bipyridyl, 0.3 g (0.002 mol) of anhydrous NiCl$_2$, 30 mL of dry, deoxygenated DMF, and 2 g of activated 3A molecular sieves. The mixture is heated under nitrogen to 65° C. until the gray color changed to dark brown (about 10–15 minutes). Maintaining a pot temperature of 60° C., a solution of (4-chloro-phenyl)-phenyl-m-tolyl amine (13.4 g, 0.04 mol) in 40 mL of DMF is added dropwise. After addition is over, the reaction is stirred between 60–65° C. for 2–5 hours, until TLC analysis revealed complete consumption of starting aryl chloride. The reaction is diluted with dichloromethane, filtered to remove excess zinc and solids. The filtrate washed four times with water. The dichloromethane layer is dried over sodium sulfate, filtered and concentrated to a reduced volume. The dichloromethane solution is treated with silica gel, filtered, and solution is treated with neutral alumina until the solution is pale yellow. The product is crystallized twice to afford 8.7 g (80%) of N$^4$,N$^{4'}$-diphenyl-N$^4$,N$^{4'}$-di-m-tolyl-biphenyl-4,4'- diamine as a white solid. An analytical sample can be obtained by chromatography using a slow gradient of 0–5% ethyl acetate in hexane.

We claim:

1. A method for synthesizing (4-chloro-phenyl)-phenyl-m-tolyl-amine (I) which comprises:
   (i) charging a nitrogen filled reactor with palladium acetate, tri-tert butyl phosphine and deoxygenated toluene;
   (ii) agitating the step (i) pale yellow reaction mixture to produce a red color and thereafter
   (iii) sequentially adding to the step (ii) red reaction mixture bromobenzene, sodium t-butoxide, and m-toluidine;
   (iv) heating the step (iii) reaction mixture to produce a step (iv) reaction mixture containing m-methylphenyl amine;
   (v) treating said step (iv) reaction mixture with sodium t-butoxide and 1,4-chlorobromobenzene, wherein a step (v) reaction mixture containing (I) is produced.

2. The method of claim 1 further comprising a step (vi) recovering (I) as a solid from said step (v) reaction mixture.

3. The method of claim 1 further comprising a step
   (vii) converting said solid (I) recovered in step (vi) to N$^4$,N$^{4'}$-diphenyl-N$^4$,N$^{4'}$-di-m-tolyl-biphenyl-4,4'-diamine (II).

4. The method of claim 3 wherein said converting step (vii) is accomplished by a nickel catalyzed coupling of (I).

5. A method of coupling (4-halo-phenyl)-phenyl-m-tolyl-amines (I) to produce N$^4$,N$^{4'}$-diphenyl-N$^4$,N$^{4'}$-di-m-tolyl-biphenyl-4,4'-diamine (II) which comprises:
   (i) charging a reactor with zinc powder, triphenylphosphine, 2,2'-bipyridyl, NiCl$_2$ and DMF, wherein a mixture of a gray color is produced;
   (ii) heating said stop (i) mixture of gray color in said step (i) reactor to produce a step (ii) mixture of dark brown color;
   (iii) adding a solution of (I) in DMF to said step (ii) mixture to produce a stop (iii) reaction mixture in said step (i) reactor; and (iv) heating said step (iii) reaction mixture, wherein a step (iv) reaction mixture containing (II) is produced.

6. The claim 5 method further comprising a step (v) recovering said (II) from said step (iii) reaction mixture.

7. A method of coupling a triaryl amine having the formula (A):

(A)

wherein $AR_1$, $AR_2$ and $AR_3$ are the same or different aryl groups, and X is a halogen wherein at least one of said aryl groups may or may not have one or more ortho, meta or para $C_1$ to $C_{10}$ alkyl substituent which comprises:

(i) charging a nitrogen filled reactor with a mixture of zinc powder, triphenylphosphines, 2,2'-bipyridyl, anhydrous $NiCl_2$ and deoxygenated DMF, wherein said mixture is gray in color;

(ii) heating said step (i) mixture in said reactor to provide a step (ii) mixture dark brown in color;

(iii) treating said step (ii) mixture in said reactor with a DMF solution of a compound of formula (A), wherein step (iii) reaction mixture containing a compound of formula (B)

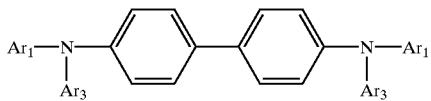
(B)

is produced.

8. A method which comprises:

(i) providing a reactor containing monomeric triaryl amine molecules having the formula (A):

(A)

wherein $AR_1$, $AR_2$ and $AR_3$ are the same or different aryl groups, and X is a halogen wherein at least one of said aryl groups may or may not have one or more ortho, meta or para $C_1$ to $C_{10}$ alkyl substituent; and (ii) subjecting said monomeric triaryl amine having the formula (A) as contained in said step (i) reactor to conditions effective to cause coupling of two of said monomeric triaryl amine molecules in said reactor, wherein a reaction mixture containing a compound of formula (B)

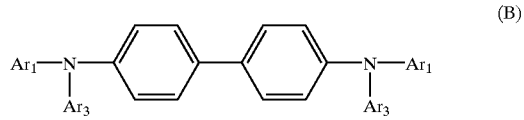
(B)

is produced in said step (i) reactor.

9. The method of claim 8, wherein said monomeric triaryl amine contained in said step (i) reactor is (4-chloro-phenyl)-phenyl-m-tolyl amine.

10. The method of claim 8, wherein said conditions effective to cause coupling comprise nickel catalysis.

* * * * *